United States Patent [19]

Pompa

[11] E Patent Number: Re. 32,680

[45] Reissued Date of Patent: May 31, 1988

[54] PROTECTIVE COVER FOR HUMAN LIMB JOINTS

[75] Inventor: Susan Pompa, Lincolnwood, Ill.

[73] Assignee: S. J. Kaplan and Associates, Inc., Lincolnwood, Ill.

[21] Appl. No.: 724,291

[22] Filed: Apr. 17, 1985

Related U.S. Patent Documents

Reissue of:

[64] Patent No.: 4,471,770
Issued: Sep. 18, 1984
Appl. No.: 404,431
Filed: Aug. 2, 1982

[51] Int. Cl.[4] ..... A61F 13/00

[52] U.S. Cl. ..... 128/132 R; 128/153;149;77;80 R

[58] Field of Search ..... 128/132 R, 153, 149, 128/77, 80 R, 80 H, 165, 166, 134, 16, 22, 24

[56] References Cited

U.S. PATENT DOCUMENTS

| | | | |
|---|---|---|---|
| 1,055,040 | 3/1913 | Herron et al. | 2/24 |
| 1,074,531 | 9/1913 | Schmitt | 2/24 |
| 1,351,731 | 9/1920 | Baldwin | 128/165 |
| 1,452,360 | 4/1923 | Clarke | 2/24 |
| 1,570,088 | 1/1926 | Buchanan | 2/24 |
| 1,587,508 | 6/1926 | Coats | 2/24 |
| 1,846,835 | 2/1932 | Bruckler | 2/62 |
| 2,270,685 | 1/1942 | Miller | 2/24 |
| 3,216,417 | 11/1965 | Posey | 128/149 |
| 3,406,683 | 10/1968 | Steinberg | 128/153 |
| 3,721,237 | 3/1973 | Alessio | 128/153 |
| 3,937,218 | 2/1976 | Gaylord, Jr. | 128/149 |

OTHER PUBLICATIONS

Richards Manufacturing Co., Inc., Orthopedic catalog, 1979, p. 44.

The Tetra Company, catalog page titled Tetra TM Decubitus Pads.

*Primary Examiner*—Edward M. Coven

*Attorney, Agent, or Firm*—Paul H. Gallagher

[57] ABSTRACT

A removable protective cover to be fitted on the limb joints, such as the elbow and the heel of a patient. It forms a generally "L" shape interior with one portion fitted over the fore arm and a portion over the upper arm. It is made of lambskin, having the leather or skin side out receiving the abrasive action from the bed (or chair), in which the patient is confined, and the wool side in, in contact with the wearer's skin. It is secured in position by quick-detachable straps that can be easily manipulated by a semi-invalid. It is made in different sizes, for adults and children, and can be used on the heel as well as the elbow.

8 Claims, 2 Drawing Sheets

Fig. 7.
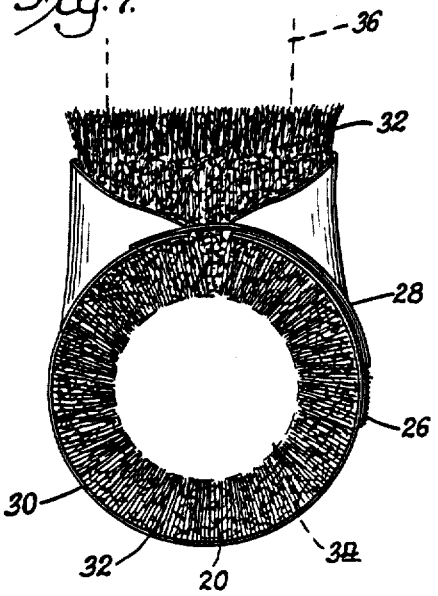
Fig. 6.
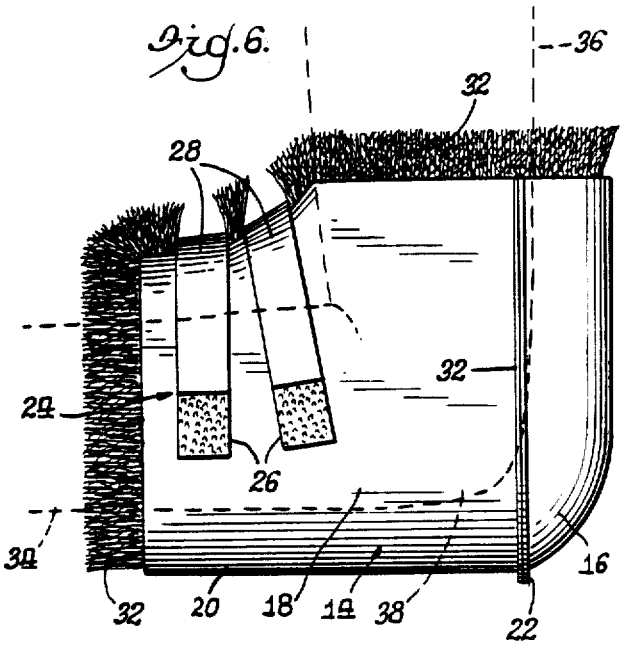
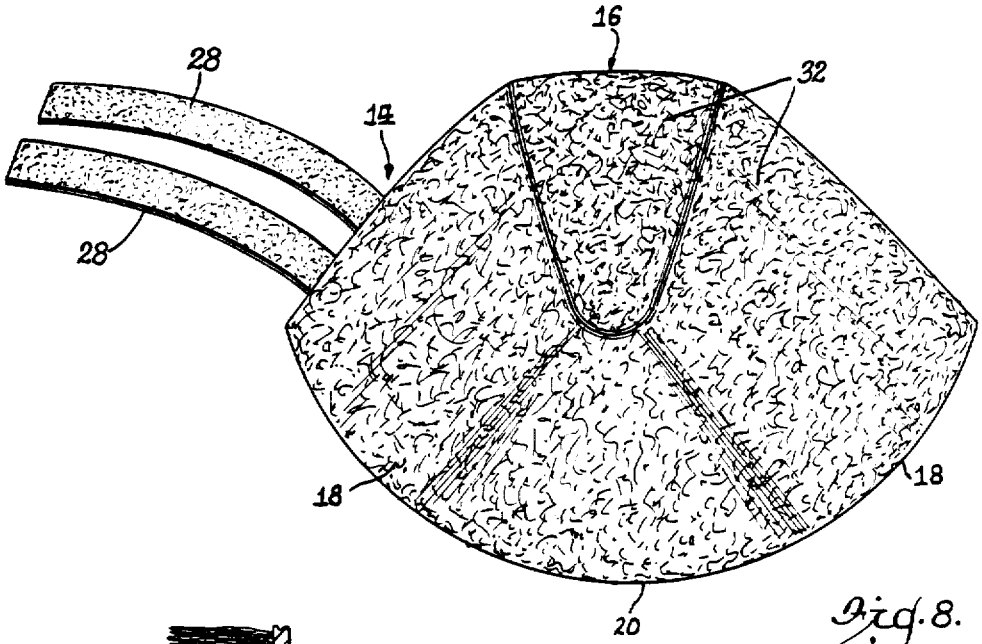
Fig. 8.
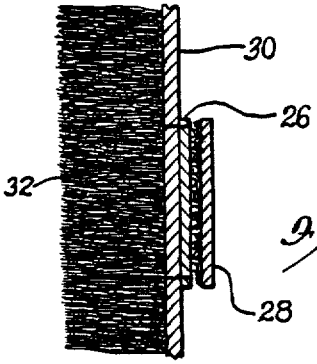
Fig. 9.

PROTECTIVE COVER FOR HUMAN LIMB JOINTS

Matter enclosed in heavy brackets [ ] appears in the original patent but forms no part of this reissue specification; matter printed in italics indicates the additions made by reissue.

FIELD OF THE INVENTION

The invention lies in the field of caring for patients who are bed-ridden, or spend considerable time in bed, including those that are confined to wheel chairs, or otherwise confined. The patient being confined, for example in bed, develops sores by contact, as in rubbing, with the bed clothes and these occur most often on the limb joints, as the elbows and the heels. These sores develop from rubbing action or abrasive action with the bed clothes, as distinguished from mere aches and pains from immobility. These sores may develop not only from bed clothes, but from other sources, such as in wheel chairs, where the elbows or heels may rest on or rub against the elements of the wheel chair, with consequent similar sores on the joints. Heretofore there had been various means and methods developed for counteracting or preventing such sores, but none of them have been entirely satisfactory, and in fact most of them have been greatly lacking in the effect desired.

OBJECTS OF THE INVENTION

A broad object of the invention is to provide a novel protector for human limb joints, such as the elbow and the heel, for use by a patient who spends considerable time in bed, or in a chair (e.g. wheel chair), having the following features and advantages:

1. It completely covers the elbow, or heel, and effectively protects the skin of the wearer from sores often acquired by patients.

2. It is made of natural lambskin, having both the leather and the wool, with the wool disposed inwardly and the leather outwardly; the wool presents a cushion effect and comfortable feeling to the wearer, and warm feeling in winter and cool feeling in summer, and the leather receives the abrasive action from the bed or chair.

3. The leather is very pliable, facilitating fitting of the cover to the patient's limb and adapting to movements of the body of the wearer.

4. It is easily applied to and removed from the elbow or the heel, by the wearer, thereby facilitating such by a semi-invalid.

5. Its design and construction facilitates making it in different sizes, for adults and for children, and for the elbow and for the heel.

*6. Its design and construction renders it more pliable, to better fit the elbow or heel.*

*7. Its design and construction renders a single and same article especially adaptable to application to either the elbow or the heel.*

DESCRIPTION OF A PREFERRED EMBODIMENT

In the drawings

FIG. 6 is a view of the device, oriented according to FIG. 3, as applied to the wearer's elbow;

FIG. 7 is a view from the left of FIG. 6;

FIG. 8 is a view of the protective cover in opened-out position, oriented in the direction of FIG. 7; and FIG. 9 is a sectional view taken at line 9—9 of FIG. 4.

In referring to the overall objectives of the device of the invention, and as referred to above, the device may be worn by the patient on the elbow or on the heel. For convenience, the elbow and the heel are referred to generically as joints in the human limbs, i.e. the arms and legs, and in either case the joint is referred to as including members disposed transversely relative to each other; for example in the case of the elbow, the members are the fore arm and the upper arm, and in the case of the heel, the members are the foot and the ankle.

Figure 1:
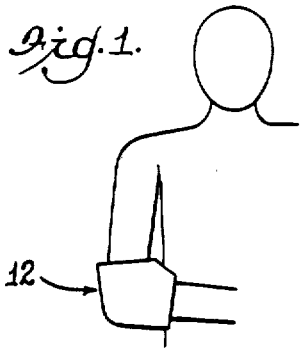
FIG. 1 is a diagrammatic sketch of a person wearing the device of the invention on his elbow.
Figure 2:
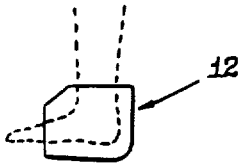
FIG. 2 is a diagrammatic sketch of the device on the wearer's heel.
Figure 3:
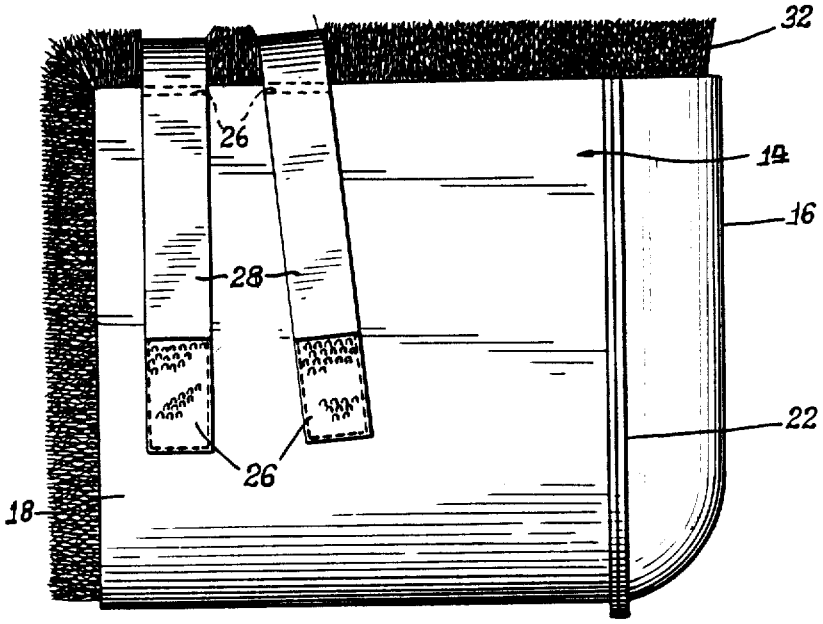
FIG. 3 is a side view of the protective cover.
Figure 4:
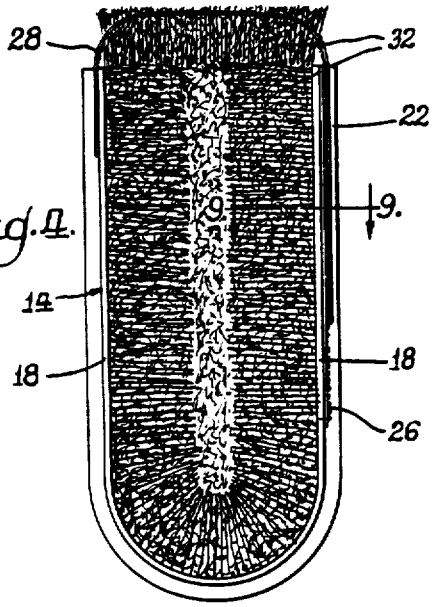
FIG. 4 is an end view from the left end of FIG. 3.
Figure 5:
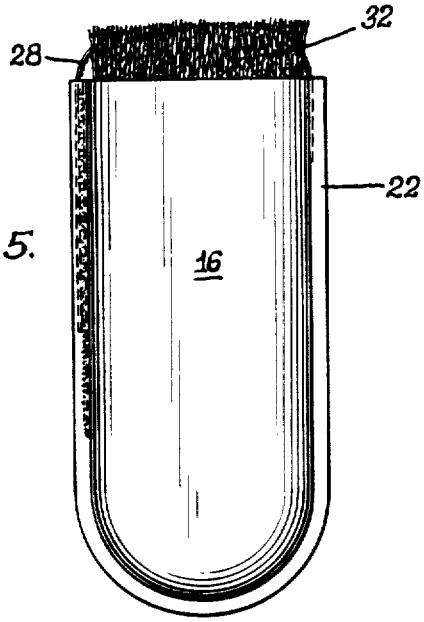
FIG. 5 is an end view from the right end of FIG. 3.

Referring in detail to the drawings, FIG. 1 shows the protective device of the invention applied to the elbow of the wearer, and FIG. 2 shows it applied to the heel. Referring particularly to FIGS. 3–5, the protective [covering] *cover* 12 is made up of two main pieces, a first piece 14 and a second piece 16. The piece 14 is the larger of the two, preferably of U-shape, having parallel legs 18, interconnecting which is a curved portion or bight 20. The second piece 16 extends transversely between the legs of the first piece, at [one] *a first* end of the latter, filling the space formed by the U-shape, and the two pieces are stitched together along a continuous seam 22. The overall shape of the cover as viewed in side view, may be generally rectangular. Securing means 24 is provided on the piece 14 adjacent *a second end, that is,* the end opposite the second piece 16 and includes preferably a type generally known as "Velcro", there being two units, each made up of a first or backing strip 26, in this case sewed directly to the corresponding side or leg 18 on the piece 14, and a strap 28 secured to the opposite leg 18. The straps 28 are thrown over the open side of the U-shaped first piece and fitted in face-to-face contact engagement with the strips 26 and are held there securely in normal usage. This type of securing means is known, and one of the pieces, such as the strips 26 have tentacles acting as "hooks" which engage and grab elements of the straps. This kind of securing means is of particular convenience for use by semi-invalids, because it is easy to manipulate, both to engage or secure, and disengage or separate. Those acts can be done easily with one hand and in most cases the patients can apply the cover themselves and need not be helped by attendants.

The protective cover 12 is made of natural lambskin. As herein used, the material will be referred to generically as hide, which is constituted by the outer covering of the animal, i.e. the lamb, and includes the leather or skin 30 and the wool 32 thereon. The protective cover is constructed with the leather or skin disposed outwardly, and the wool inwardly. It is applied to the joint, i.e. the elbow, (FIG. 6) by fitting the legs 18 of the U-shaped piece 14 against the fore arm 34, and the second piece 16, at the end fitted against the upper arm 36, the elbow proper being indicated at 38. After the cover is thus fitted to the elbow, the straps 28 of the securing means are flapped or fitted down against the backing strips 26 and are securely held thereby, as noted above. In this step, the top edges of the legs 18 of the U-shaped first piece, are folded around the fore arm, or partially so, according to the various dimensions involved, and the extent to which the wearer manipulates the elements. In its position as thus applied, the cover is generally "L" shape, forming in effect two openings disposed transversely relative to each other, receiving the fore arm and the upper arm, themselves generally transverse to each other, and it is thereby securely held in place on the elbow. The straps 28 are of substantial length, and can overlap the backing strips a greater or lesser amount, thereby providing a wide range of adjustability for different size areas.

The protective cover may be of any size desired, both as to size of person, and the manner in which it is to be fitted on the elbow. Since the wool is positioned inwardly, it engages the skin of the wearer and provides a cushion for the elbow, and the arm. For example the wool may be of a thickness of about ¾ of an inch, i.e. inwardly from the skin or leather and this great depth obviously provides great comfort to the wearer. The leather being on the outside, absorbs the abrasive action in engaging the bed or chair, this arrangement providing great comfort to the wearer, and long life to the device, the leather being highly wear resistant.

Wool has an added advantage in the comfort of the wearer, in that it is not only warm in the winter time, but is actually cool in the summer, the wool absorbing the perspiration from the wearer and enabling air to pass through the strands of the wool to produce a cooling effect.

The skin of the hide is very soft and pliable. It is tanned to accomplish that end, and it thereby adapts itself well to the shape and size of the patient's limb joint. Also, for example, the cover may not be put on exactly straight or symmetrically, but will nevertheless adapt itself well to the joint because of its pliability. Furthermore, as the arm is bent or flexed, the cover adapts itself to such movements, shifting according to the positioning or movements of the limb members. Moreover, the softness and pliability of the leather facilitates applying the device in position. For example, a semi-invalid may find it difficult to actually apply the cover and move the securing strips down into securing position, but the pliability of the leather makes it easy to shape it to the arm and in this way facilitates putting the securing strips down into securing position.

Different forms of tanning the leather may be utilized, selectively, such as the gluteraldehyde process, or chrome tanning. Gluteraldehyde tanning imparts a very desirable characteristic—washability. It can be dried in a dryer for longer time than regular lambswool.

A further advantage of the device is that wool, in its natural condition, greatly resists combustion.

*The construction of the protective cover renders it especially adaptable to either the elbow or the heel, particularly in that the legs 18 of the U shape piece 14 have substantial length, in direction perpendicular to the bight 20, relative to the dimension between the legs, so that the legs, and the piece 16, in that direction, provide substantial coverage of corresponding member of the limb of the wearer. Similarly, the legs 18 have a substantial second length in direction parallel with the bight 20, so that the legs 18 provide substantial coverage in that direction, along the respective member of the limb. In each case, the elements of the protective cover reach a substantial distance along the length of the limb member, as well as a substantial extent around it, and in both cases all parts of the cover are effectively held by the securing means at one location, that is, the securing elements 26, 28 across the legs 18. Additionally, the parts of the cover accommodate the limb members in different relative angular positions of the limb members.*

*For convenience in identification of the various elements of the protective cover, and considering a feature implicit in the original disclosure, the lambskin may be referred to as a fleece, this being used as a generic term herein, having a base corresponding to the leather and fibers corresponding to the wool on the leather.*

*The design and construction as described above is well adapted to the use of materials other than lambskin, such as synthetic materials, in which a fabric is used as a base, corresponding to the leather, and synthetic fibers or filaments thereon corresponding to the wool.*

I claim:

1. A protective cover adapted to be applied to a human limb joint such as the elbow or the heel, the limb having members directed generally transversely relative to each other, and the cover when so applied to the limb joint having relationship thereto as set out hereinbelow, the protective cover comprising, a natural hide composed of a leather layer and a wool layer thereon, including a first elongated piece and a second piece, said first piece having opposite, substantially parallel, longitudinal marginal edges and opposite terminal edges and being of generally U-shape form about a longitudinal axis, forming parallel leg portions of substantial length along said axis, and of substantial width transverse thereto, the legs thereby being of great area, said first piece defining opposite open ends bound by said marginal edges, said second piece being positioned transversely across one of said open ends of the first piece and secured thereto continuously around the marginal edge of the U-shape of the first piece, the pieces being positioned with the leather layers disposed outwardly and the wool layers disposed inwardly, and the layers extending throughout the areas of the respective pieces, said leg portions being adapted to be fitted to opposite sides of the limb, and said second piece being adapted to engage the corresponding surface of an adjacent limb member, said second piece and the adjacent elements of said leg portions effectively surrounding one of the limb members and forming an opening through which that limb member extends, and the leg portions of said first piece effectively surrounding the other of the limb members and forming an opening through which that limb member extends, and the cover effectively enclosing the portion of the limb between the openings, and releasable securing means including a plurality of straps fixedly secured to the outer surface of one of said leg portions at a position remote, in axial direction, from said second piece, each strap extending from the terminal edge of said one leg portion to the terminal edge of the opposite of said leg portions when in securing position, and being releasably secured to the outer surface of said opposite leg portion whereby, the securing means being operable for effecting the surrounding condition of the leg portions relative to the respective limb member, and also operable for effecting the surrounding condition of the leg portions and the second piece together relative to the respective limb member, said first piece and said second piece constituting the entire cover, except for the securing means, and thereby extending throughout the area of the protective cover, the leather layer being exposed, except for the location of the securing means, throughout its area and devoid of any other matèrials, and thereby forming the only surface that engages other objects in the wearing of the protective cover, and the wool being exposed throughout its area and devoid of any other materials, and thereby forming the only surface that engages the limb of the wearer.

2. A protective cover according to claim 1 wherein, the leather is of a gluteraldehyde-tanned condition.

*3. A protective cover adapted to be applied to a human limb joint such as the elbow or the heel, the limb having members directed generally transversely relative to each other, comprising,*

*a fleece incorporating a base and fibers thereon, and including a first piece and a second piece, originally independent of and separate from each other,*

*the first piece being of U shape formation, and including a pair of parallel legs and a bight interconnecting the legs, the legs being thereby spaced apart and the first piece defining a first open end and a second open end, and having a marginal edge of U shape at each end, said legs extending circumferentially at least a portion of one of the members of the wearer's limb,*

*the second piece being positioned transversely across the space between the legs at said first end and secured to the first piece at the corresponding marginal edge of the latter,*

*the fleece being oriented with the fibers directed inwardly to engage the wearer's limb, and the base directed outwardly, and*

*releasable securing means on the first piece including interconnectable elements on respective ones of the legs thereof, certain of said elements extending over and across said space when the elements are respectively interconnected,*

*said first and second pieces constituting, except for said securing means, the entire protective cover, and constituting the entire portions engagable with the wearer's limb, and the entire portions having exterior surfaces engaging external objects which the wearer's limb engages, the fibers being distributed throughout the area of the base.*

*4. A protective cover according to claim 3 wherein, said legs of the first piece are of substantial length in direction perpendicular to said bight and thereby capable of extending a substantial distance around the wearer's limb, and*

*the securing means includes elements readily manipulatable by one hand, and put in securing position by pressing them together in direction transverse to the direction of the tendency to pull apart and releasable by pulling them in direction opposite the pressing direction.*

*5. A protective cover according to claim 4 wherein,*

*said first piece is of substantial length in direction parallel with said bight,*

*said securing means is positioned in spaced relation to said first end and thereby to said second piece, the second piece and the portions of the legs of the first piece next adjacent the second piece, are free of securing means, and said second piece and those portions of the legs define an opening surrounding and accommodating the other member of the limb.*

*6. A protective cover according to claim 3 wherein,*

*the second piece covers the entire area between the legs of the first piece, and the two pieces terminate upwardly at a position adjacent each other.*

*7. A protective cover according to claim 6 wherein,*

*the pieces are secured together by stitching the bases of the pieces together.*

*8. A protective cover according to claim 7 wherein,*

*the stitching extends entirely around the U shape linearly throughout the legs and the bight therebetween.*

* * * * *